United States Patent [19]

Knosp

[11] 4,179,286
[45] Dec. 18, 1979

[54] SILVER FREE, LOW GOLD-NOBLE METAL ALLOYS FOR FIRING OF DENTAL PORCELAIN

[75] Inventor: Helmut Knosp, Pforzheim, Fed. Rep. of Germany

[73] Assignee: Deutsche Gold- und Silber-Scheideanstalt vormals Roessler, Frankfurt, Fed. Rep. of Germany

[21] Appl. No.: 4,191

[22] Filed: Jan. 17, 1979

[30] Foreign Application Priority Data

Mar. 31, 1978 [DE] Fed. Rep. of Germany ....... 2813813

[51] Int. Cl.$^2$ .......................... C22C 5/02; C22C 5/00
[52] U.S. Cl. .............................. 75/134 N; 75/134 T; 75/134 B; 75/165; 75/172 G; 75/172 R
[58] Field of Search ............ 75/134 N, 134 T, 134 B, 75/165, 172 R, 172 G, 134 G

[56] References Cited

U.S. PATENT DOCUMENTS

| | | | |
|---|---|---|---|
| 3,134,671 | 5/1964 | Prosen | 75/172 |
| 3,666,540 | 5/1972 | Burnett | 117/129 |
| 3,667,936 | 6/1972 | Katz | 75/134 N |
| 3,716,356 | 2/1973 | Burnett | 75/165 |
| 3,819,366 | 6/1974 | Katz | 75/172 R |
| 3,981,723 | 9/1976 | Tuccillo | 75/165 |
| 4,123,262 | 10/1978 | Cascone | 75/165 |

*Primary Examiner*—L. Dewayne Rutledge
*Assistant Examiner*—Upendra Roy
*Attorney, Agent, or Firm*—Cushman, Darby & Cushman

[57] ABSTRACT

A silver free, low gold, noble metal alloy for firing on dental porcelain is prepared consisting of 30 to 55% gold, 30 to 60% palladium, 1 to 12% tin, 0 to 10% indium, 0.1 to 3% germanium, and 0.05 to 1% rhenium and/or 0.05 to 1% ruthenium.

10 Claims, No Drawings

SILVER FREE, LOW GOLD-NOBLE METAL ALLOYS FOR FIRING OF DENTAL PORCELAIN

BACKGROUND OF THE INVENTION

The invention is directed to silver free, relatively low gold noble metal alloys for firing on dental porcelain which above all contain gold, palladium, tin and, in a given case, indium.

Noble metal alloys are used in dentistry. Crowns and bridges are made from such alloys by the wax melting process and subsequently are coated with porcelain. While the metal framework provides for the stability of the crowns or bridges, the particular tissue compatible accepted porcelain seeks to reproduce the function, color and shape of the natural teeth.

The connection between alloy and porcelain requires a coordination in the physical and mechanical properties of both. Both work materials above all must agree in their coefficient of thermal expansion as well as in their modulus of elasticity. Besides the alloy should be able to be worked up without problem by casting technology. Therefore, it is required that the melting range not be too elevated. On the other hand, the heat resistance must be sufficient that at the firing temperature of the porcelain there does not occur any sagging of the framework. The alloy furthermore should be in a position to form suitable oxides on its surface which brings about the adhesion to the porcelain. Reactions between these adhesive oxides and the oxide constituents of the porcelain during the process are highly undesirable because there occur particular colorations of the porcelain composition through them.

There are already known noble metal alloys for the metal ceramics in dentistry, for example made from 70 to 90% gold, 5 to 15% platinum, 0.5 to 10% palladium, 0.1 to 2% indium, 0.1 to 2% tin, and 0.05 to 1% of rhenium (German Pat. No. 1,533,233). Furthermore, they can contain up to 5% silver, up to 1% copper, 0.05 to 0.5% iridium and/or up to 0.5% of zinc.

Furthermore, there are known noble metal alloys for firing on dental porcelain which contain substantially less or even no gold, but instead contain chiefly palladium and silver. According to German OS 2,440,425, such alloys consist essentially of 0 to 45% gold, 25 to 60% palladium and 15 to 45% silver. They can also contain additives of copper, iron, iridium, rhenium, tin, indium, and zinc.

These alloys, which above all, because of the high price of gold, are substantially cheaper than the previously mentioned high gold containing alloys are characterized above all by high silver contents. The high silver content in these low gold alloys particularly is made possible by the fact that gold can be relatively simply replaced by silver without substantially influencing the processing properties of the alloy in regards to casting technology. On account of the relatively low melting point of silver, it does not increase the melting range of alloys in which gold is replaced by silver so that even the meltability of these alloys is not impaired.

However, a disadvantage of these high silver containing alloys is the high coefficient of thermal expansion of silver. In comparison to the average linear coefficients of thermal expansion for example of gold ($15.7 \times 10^{-6}$/K at 600° C.) and of palladium ($13.6 \times 10^{-6}$/K at 600° C.) that of silver is substantially higher, being $21.3 \times 10^{-6}$/K at 600° C. (VDI-Richtlinien 3128, Physikalische Stoffeigenschaften der reinen Metalle, Sheet 2, October, 1977). This also has an effect on the coefficients of thermal expansion of high silver content alloys in which a harmonizing with the coefficients of thermal expansion of commercial porcelain compositions ($21 - 13 \times 10^{-6}$/K) is either attained only with great difficulty or not at all.

Further, in using high silver content firing on alloys, during the firing of the porcelain there cannot be avoided the possibility of reactions of the silver with the porcelain which lead to an extremely disturbing discoloration of the porcelain. It is believed that the silver oxide forms mixed oxide with the oxides in the porcelain, which similar to the melt colors in porcelain glazes show characteristic colors. While with silver containing alloys there occur brown discolorations of the porcelain, with copper containing alloys, green discolorations are observed (Guide to Dental Materials and Devices, 6th edition, American Dental Association, pages 36 to 37, 1972 to 1973).

The aesthetics of porcelain faced crowns and bridges is impaired considerably by this kind of discoloration.

The problem of the present invention therefore was to create noble metal alloys for the firing on of dental porcelain which contain no silver and no copper and simultaneously have good processing properties in regard to casting technology, as well as harmonizing with the commercial fired on porcelain compositions, particularly in regard to the coefficients of thermal expansion.

SUMMARY OF THE INVENTION

This problem was solved by using noble metal alloys which contain besides 30 to 55% gold, 30 to 60% palladium, 1 to 12% tin, and 0 to 10% indium, and, in accordance with the invention contain 0.1 to 3% germanium, 0.05 to 1% of rhenium and/or 0.05 to 1% ruthenium.

It has been found unexpectedly that by the addition of germanium to the gold-palladium-tin alloys, which can also have indium present, there are produced firing on alloys whose melting ranges are not too high and therefore cause no problems in casting technology. It has proven particularly surprising that the known reduction of the melting range of noble metal alloys by tin and indium undergoes a considerably greater effect if there is also added germanium. This is therefore of especial significance, because too high tin or indium content leads to embrittlement of the alloys. Therefore, by using germanium, the content of tin or indium can be reduced.

As particularly advantageous, it has unexpectedly been shown that in the alloys of the invention, additions of rhenium and/or ruthenium cause a very fine-grained structure. The maximum effect in particle size reduction is obtained by the combination of the alloy constituents of the invention when the weight ratio of germanium to rhenium and/or ruthenium is from 2 to 3:1.

By the addition of germanium rhenium and/or ruthenium according to the invention, the remaining properties of the fired on alloys are not influenced unfavorably. The mechanical properties such as hardness, yield strength, tensile strength and elongation even surpass those of the known silver containing fired on alloys.

Silver and copper containing noble metal alloys, particularly at low gold contents often tarnishes in the mouths of patients. Therefore, it is possible to use the alloys of the invention as tarnish resistant casting alloys for inlays, crowns and bridges or to use them in combination with synthetic resin facings.

Unless otherwise indicated, all parts and percentages are by weight.

The alloys can consist essentially of or consist of the stated materials.

DESCRIPTION OF THE PREFERRED EMBODIMENTS

Several examples of the composition of the silver-free noble metal alloys with additions of germanium and rhenium and/or ruthenium are given in the following table.

TABLE

| Example Number | Composition Proportions in % | | | | | | | Melting Range °C. | | Hardness Hv | |
|---|---|---|---|---|---|---|---|---|---|---|---|
| | Au | Pd | Sn | In | Ge | Re | Ru | | | soft | aged |
| 1 | 53.9 | 31 | 5.5 | 9.45 | 0.1 | 0.05 | — | 1240 | 1120 | 215 | 345 |
| 2 | 49 | 35 | 9 | 5 | 1.5 | 0.45 | 0.50 | 1260 | 1160 | 200 | 325 |
| 3 | 47 | 39 | 4 | 8 | 1.4 | 0.6 | — | 1280 | 1170 | 185 | 255 |
| 4 | 45 | 42 | 1 | 9.3 | 1.8 | 0.9 | — | 1295 | 1165 | 170 | 270 |
| 5 | 42 | 46.7 | 7.5 | 0.5 | 2.3 | — | 1.0 | 1280 | 1145 | 160 | 245 |
| 6 | 41 | 47.8 | 10.9 | — | 0.2 | 0.1 | — | 1310 | 1170 | 195 | 310 |
| 7 | 40 | 46 | 12 | 1.6 | 0.3 | — | 0.1 | 1290 | 1140 | 210 | 355 |
| 8 | 37 | 48 | 11 | 2.2 | 1.2 | 0.3 | 0.3 | 1285 | 1165 | 205 | 360 |
| 9 | 35 | 53 | 9 | — | 2.1 | 0.4 | 0.5 | 1305 | 1180 | 185 | 305 |
| 10 | 33 | 56 | 7.4 | — | 2.7 | 0.6 | 0.3 | 1315 | 1200 | 165 | 240 |
| 11 | 31 | 59 | 6 | — | 3 | 1 | — | 1330 | 1210 | 150 | 220 |

What is claimed is:

1. A silver-free, low gold, noble metal alloy suitable for firing on dental porcelain consisting essentially of 30 to 55% gold, 30 to 60% palladium, 1 to 12% tin, 0 to 10% indium, 0.1 to 3% germanium and at least one member of the group consisting of 0.05 to 1% rhenium and 0.05 to 1% ruthenium.

2. An alloy according to claim 1 wherein the weight ratio of germanium to the total of rhenium and ruthenium is from 2 to 3:1.

3. An alloy according to claim 1 wherein the total of rhenium and ruthenium is 0.05 to 1%.

4. An alloy according to claim 3 free from indium.

5. An alloy according to claim 3 containing indium.

6. An alloy according to claim 5 wherein the indium is 0.05 to 9.45%.

7. An alloy according to claim 3 consisting of 31 to 53.9% gold, 31 to 59% palladium 1 to 12% tin, 0 to 9.45% indium 0.1 to 3% germanium and the total of rhenium and ruthenium is 0.05 to 1%.

8. An alloy according to claim 3 free from rhenium.

9. An alloy according to claim 3 free from ruthenium.

10. An alloy according to claim 3 containing both rhenium and ruthenium.

* * * * *